(12) United States Patent
Owens et al.

(10) Patent No.: US 6,592,000 B1
(45) Date of Patent: Jul. 15, 2003

(54) STERILIZATION CONTAINER FOR MEDICAL INSTRUMENTATION HAVING A SLIDING LATCH

(75) Inventors: Daniel Owens, Silver Lake, IN (US); Thomas J. Bussell, Warsaw, IN (US)

(73) Assignee: Paragon Medical, Inc., Pierceton, IN (US)

( * ) Notice: Subject to any disclaimer, the term of this patent is extended or adjusted under 35 U.S.C. 154(b) by 0 days.

(21) Appl. No.: 09/494,560

(22) Filed: Jan. 31, 2000

(51) Int. Cl.[7] .............................. B65D 6/00; B65D 45/16
(52) U.S. Cl. ........................ 220/324; 220/4.22; 292/10
(58) Field of Search .............................. 220/324, 281, 220/314, 315, 322, 323, 326, 4.22; 70/63, 67, 68, 70, 159, 160; 292/10, 33, 32, 163, 137.337

(56) References Cited

U.S. PATENT DOCUMENTS

| | | | |
|---|---|---|---|
| 195,117 A | * 9/1877 | Frankel | 392/83 |
| 1,975,173 A | * 10/1934 | Pennock et al. | 206/232 |
| 2,656,206 A | * 10/1953 | Piker | 292/86 |
| 3,339,956 A | * 9/1967 | Bencene et al. | 292/127 |
| 4,625,885 A | 12/1986 | Nichols | |
| 4,704,254 A | 11/1987 | Nichols | |
| 4,817,799 A | * 4/1989 | Gregerson et al. | 220/326 |
| 4,915,913 A | 4/1990 | Williams et al. | |
| 4,974,740 A | * 12/1990 | Niles et al. | 220/324 |
| 5,098,676 A | 3/1992 | Brooks, Jr. | |
| 5,131,558 A | * 7/1992 | Hiromori | 220/326 |
| 5,156,293 A | * 10/1992 | Petterson et al. | 220/326 |
| 5,340,551 A | 8/1994 | Berry, Jr. | |
| D350,398 S | 9/1994 | Campbell et al. | |
| 5,346,677 A | 9/1994 | Risk | |
| 5,348,185 A | 9/1994 | Buckner, III et al. | |
| 5,352,416 A | 10/1994 | Wagner | |
| 5,370,081 A | * 12/1994 | Gordon | 220/323 |
| 5,407,648 A | 4/1995 | Allen et al. | |
| 5,424,048 A | 6/1995 | Riley | |
| 5,433,929 A | 7/1995 | Riihimaki et al. | |
| 5,441,707 A | 8/1995 | Lewis et al. | |
| 5,460,288 A | * 10/1995 | Balzeau | 220/326 |
| 5,490,975 A | 2/1996 | Dane | |
| 5,508,006 A | 4/1996 | Gabele et al. | |
| 5,518,115 A | 5/1996 | Latulippe | |
| 5,524,755 A | 6/1996 | Deeds | |
| 5,525,314 A | 6/1996 | Hurson | |
| 5,628,970 A | 5/1997 | Basile et al. | |
| 5,641,065 A | 6/1997 | Owens et al. | |
| 5,682,910 A | * 11/1997 | Kizawa et al. | 132/293 |
| 5,706,968 A | * 1/1998 | Riley | 220/326 |
| 5,732,821 A | 3/1998 | Stone et al. | |
| 5,791,472 A | 8/1998 | Davis | |
| 5,823,340 A | 10/1998 | Maihofer | |
| 5,887,745 A | * 3/1999 | Wood | 220/326 |
| 5,947,462 A | * 9/1999 | Roussel | 220/324 |
| 6,012,577 A | 1/2000 | Lewis et al. | |
| 6,253,947 B1 | * 7/2001 | Yang | 220/324 |

* cited by examiner

Primary Examiner—Stephen K. Cronin
Assistant Examiner—Niki M. Eloshway
(74) Attorney, Agent, or Firm—Baker & Daniels

(57) ABSTRACT

A container having a base and a removable lid. Latches are attached to the lid for securing the lid to the base. Each latch includes a guide part secured to the lid and a slide part guided by the guide part between a closed position engaging the base and an open position spaced from the base.

14 Claims, 5 Drawing Sheets

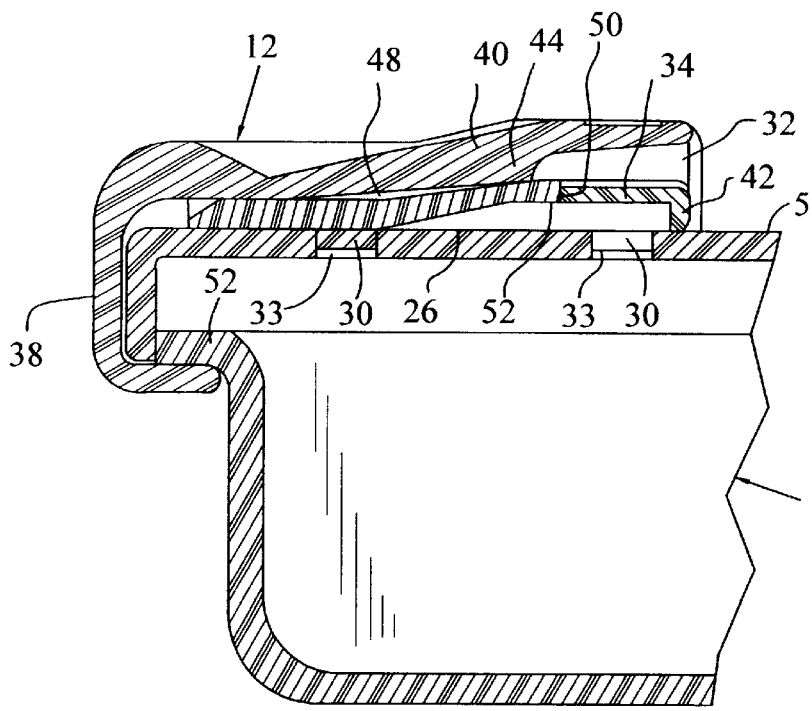
FIG. 4
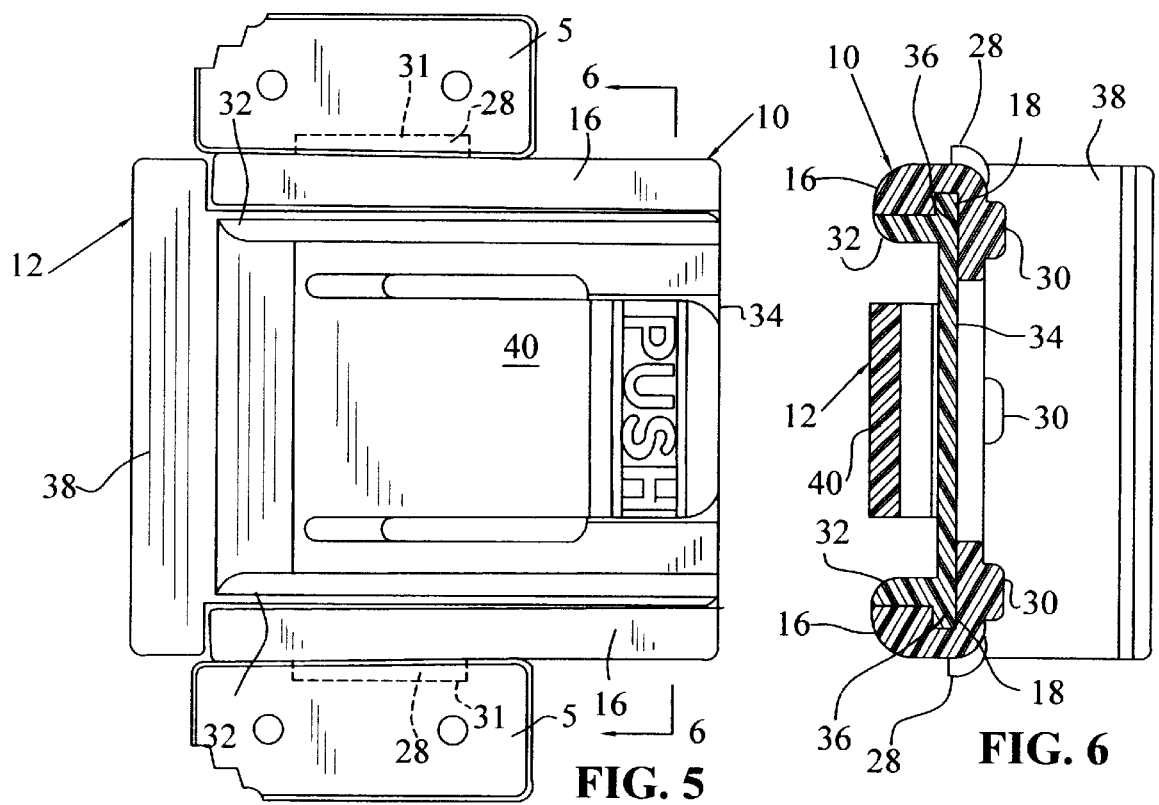
FIG. 5
FIG. 6

STERILIZATION CONTAINER FOR MEDICAL INSTRUMENTATION HAVING A SLIDING LATCH

This invention relates to a latching mechanism for the purpose of securing a lid to a container base and has specific but not limited application to a sliding latch usable with sterilization containers for such things as medical instrumentation.

Most latch mechanisms for sterilization containers and instrument containers are of metallic manufacture and generally of an over center type of operation. Some latches have sharpened edges which can cause tearing of a sterile barrier or a gloved hand and are not easily opened in medical situations where many times time is critical. In this invention a slide latch is provided. The latch includes a guide part which is secured to the lid of the container and an interfitting slide part which moves relative to the guide part. The slide part of the latch mechanism includes a depending inturned lip which when the slide part is retracted fits over the container base serving to secure the lid to the base. The guide and slide parts of the latch mechanism are preferably formed of an injection molded plastic such as polyphenylsulfone. The latch assembly may be of a specific color so as to identify the type of instrumentation or purpose of the container. Also, the latch mechanism can be easily and simply secured to the lid of the container by a snap fit interconnect.

Accordingly, it is an object of this invention to provide unique latching mechanism by which the lid may be secured to a base of a container.

Another object of this invention is to provide a sliding latch mechanism for a sterilization or medical instrumentation container.

Still another object of this invention is to provide a latch mechanism for a medical instrumentation container which is of economical construction.

And, still another object of this invention is to provide a sliding latch mechanism for a sterilization container which is of a simplified and reliable operation.

Other objects of this invention will become apparent upon a reading of the following description.

BRIEF DESCRIPTION OF THE DRAWINGS

A preferred embodiment of this invention has been chosen for purposes of illustration and description wherein:

FIG. 4 is a fragmentary sectional view as seen along line 4—4 of FIG. 1 and showing the latch mechanism in its secured or closed position.

FIG. 5 is a top plan view of the latch mechanism shown in its closed or secured position.

FIG. 6 is a cross sectional view taken along line 6—6 of FIG. 5.

DETAILED DESCRIPTION OF THE PREFERRED EMBODIMENT

A preferred embodiment of this invention has been chosen for purposes of illustration and description to enable one having an ordinary skill in the art to utilize the invention.

Figure 1:
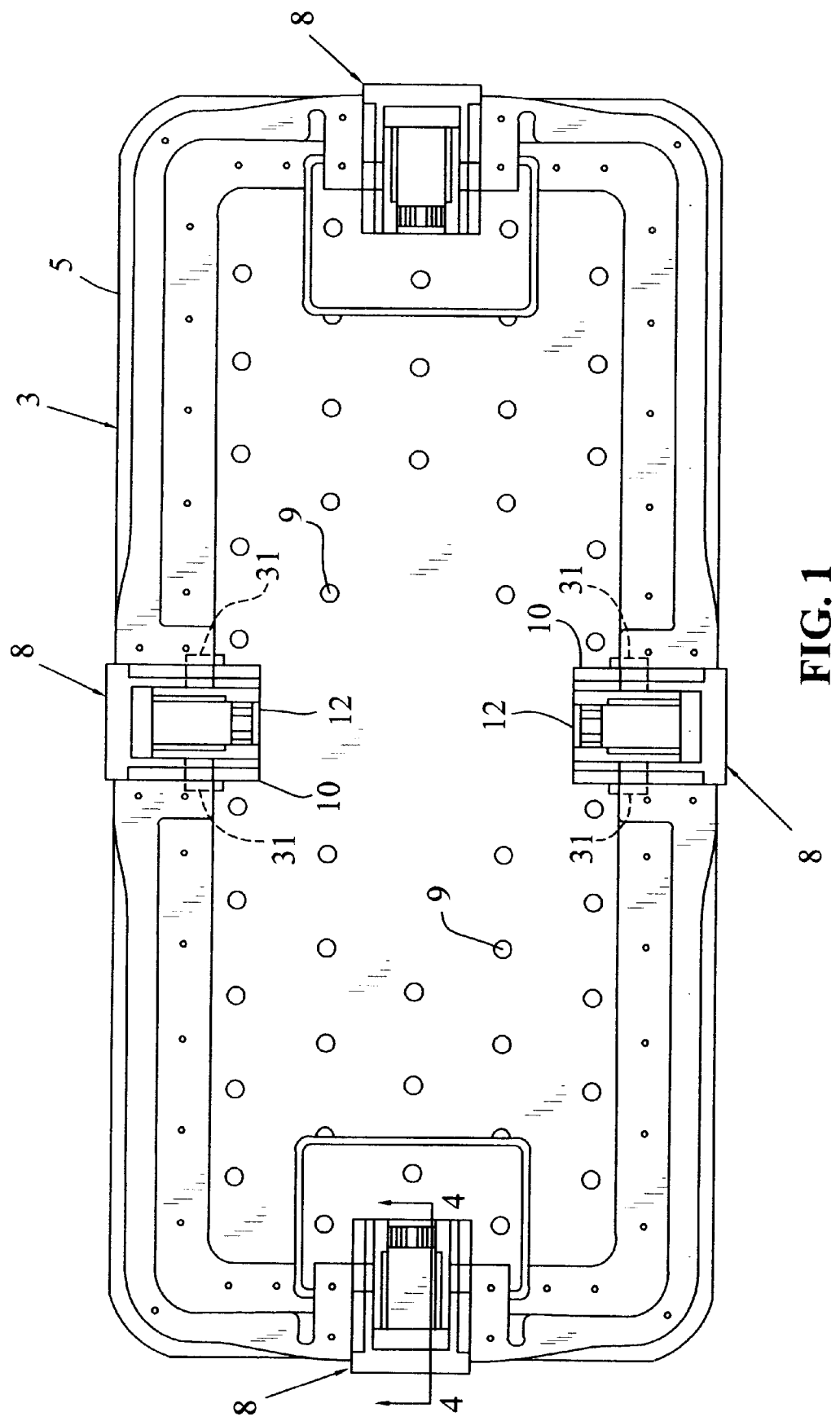
FIG. 1 is a top plan view of a sterilization container showing the latch mechanisms of this invention in use.
Figure 2:
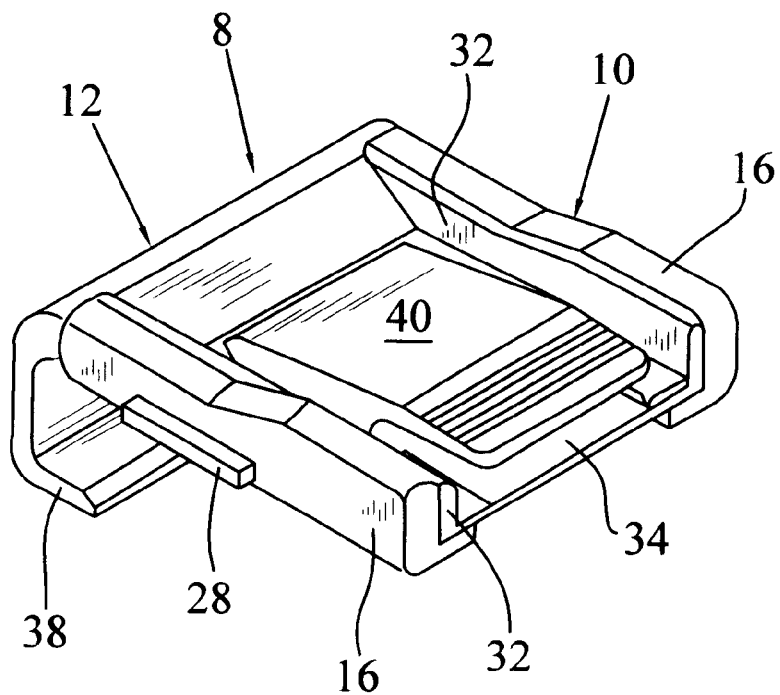
FIG. 2 is a perspective view of a latch mechanism shown in assembled form.

The latch mechanism 8 of this invention is shown in FIG. 1 being utilized upon a sterilization container 3. Container 3 includes a top or lid 5 and a bottom or base 7 (FIG. 4). The form and style of container 3 may vary but will consist of a base and an overfitting lid which may be of a metallic or plastic composition. Normally there is at least one latch mechanism 8 positioned along each side of the container so that the lid is securely fastened to the base on each of its sides. If the container is being utilized as a sterilization devise, there will be a plurality of openings 9 formed in the base and lid to allow for the escape and passage for the sterilization material such as steam.

Latch mechanism 8 includes a guide part 10 and interfitting slide part 12. Guide part 10 is secured to lid 5 and includes a base 14 which extends between a pair of side rails 16. Each of the side rails 16 forms in conjunction with base 14 a groove 18 which extends from the front 20 of the guide part to adjacent but slightly spaced inwardly from the rear 22 of the part. Base 14 of guide part 10 has a slot 24 which extends inwardly from rear 22. A flap 26 which is connected to base 14 extends upwardly and over slot 24. Flap 26 is of a flexible form which enables it to be depressed resiliently downwardly into slot 24.

Guide part 10 may be secured to lid 5 by gluing, bonding, or ultrasonic welding. Preferably, though, the guide part is designed to be snap fitted and interlocked with the lid. This is accomplished by providing transversely extending tabs 28 which protrude from slide rails 16. The underside of base 14 is provided with a plurality of posts 30. Lid 5 is provided with opposed and spaced apart slots 31 (see FIGS. 5 and 8) and openings 33 (see FIGS. 4 and 7). The guide part is pressed downwardly upon lid 5 with its posts 30 aligning with openings 33 in the lid and with its tabs 28 snap fitting into slots 31 in the lid so as to interlock the guide part to the lid. The interfit between the tabs 28 and the receiving slots 31 in the lid prevent the guide part from being lifted from the lid and the posts 30 fitting into receiving openings 33 in the lid prevent the guide part from twisting or sliding relative to the lid.

Figure 9:
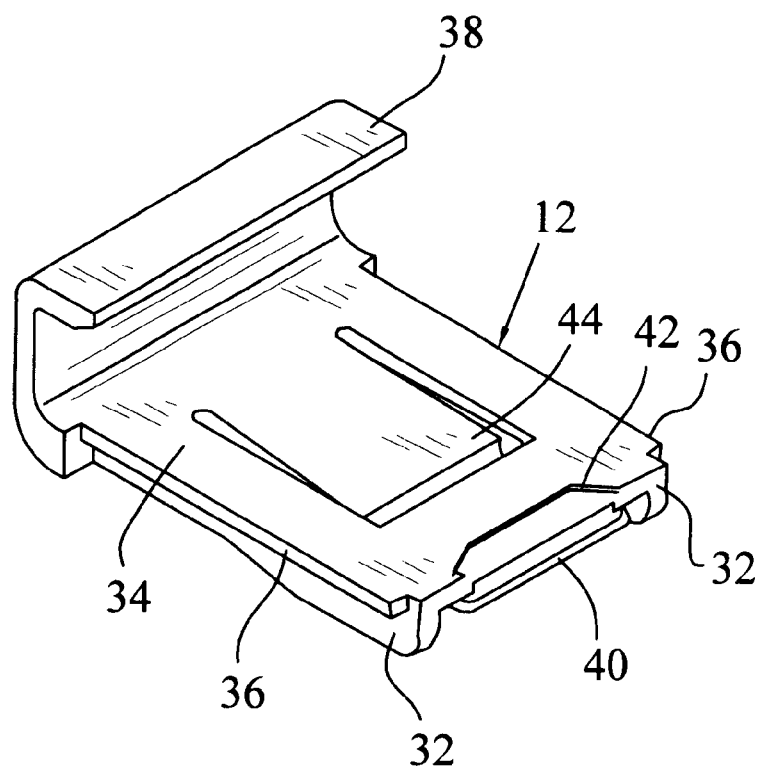
FIG. 9 is a perspective view of the guide part of the latch mechanism as seen from its underside.

Slide part 12 of latch mechanism 8 includes sides 32 which are interconnected by a web 34. A rib 36 extends along each of the sides 32. A depressible tongue 40 is carried by web 34 and protrudes or extends rearwardly relative to the slide part. Tongue 40 includes a depending protrusion 44. Web 34 terminates in a depending lip 42 (FIGS. 4 and 9). Slide part 12 also includes a forwardly located depending inturned lip 38.

Figure 3:
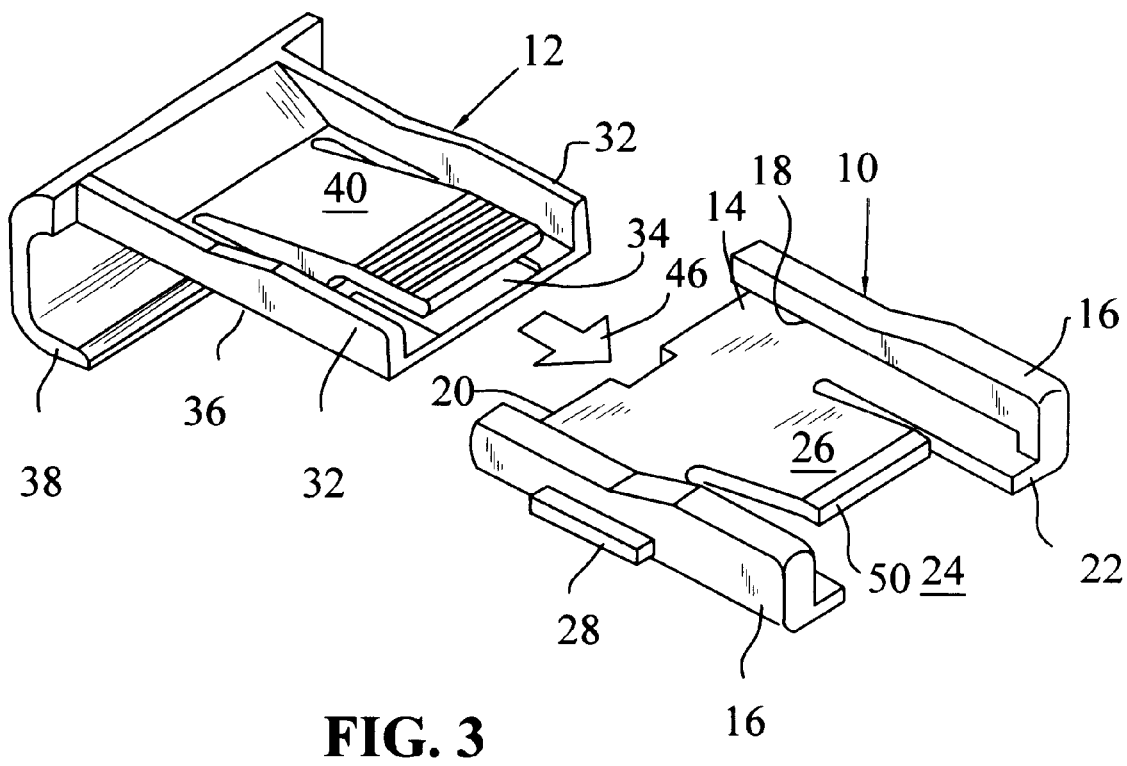
FIG. 3 is a perspective view of a latch mechanism showing its components in separated form.

Slide part 12 is assembled to guide part 10 by positioning web 34 of the slide part on top of base 14 of the guide part at front 20 of the guide part with rails 36 fitting into grooves 18. Slide part 12 is then slid rearwardly relative to the guide part in the direction of arrow 46 in FIG. 3 to cause rear lip 42 of the slide part to ride upwardly and over flap 26 of the guide part, causing the flap to be depressed until lip 42 is located rearwardly of the flap which allows the flap to spring upwardly interlocking the guide and slide parts together. This interlock between the slide part 12 and guide part 10 is best illustrated in FIG. 7 where it will be observed that flap 26 resides just under web 34 of the slide part in front of its depending rear lip 42.

Figure 7:
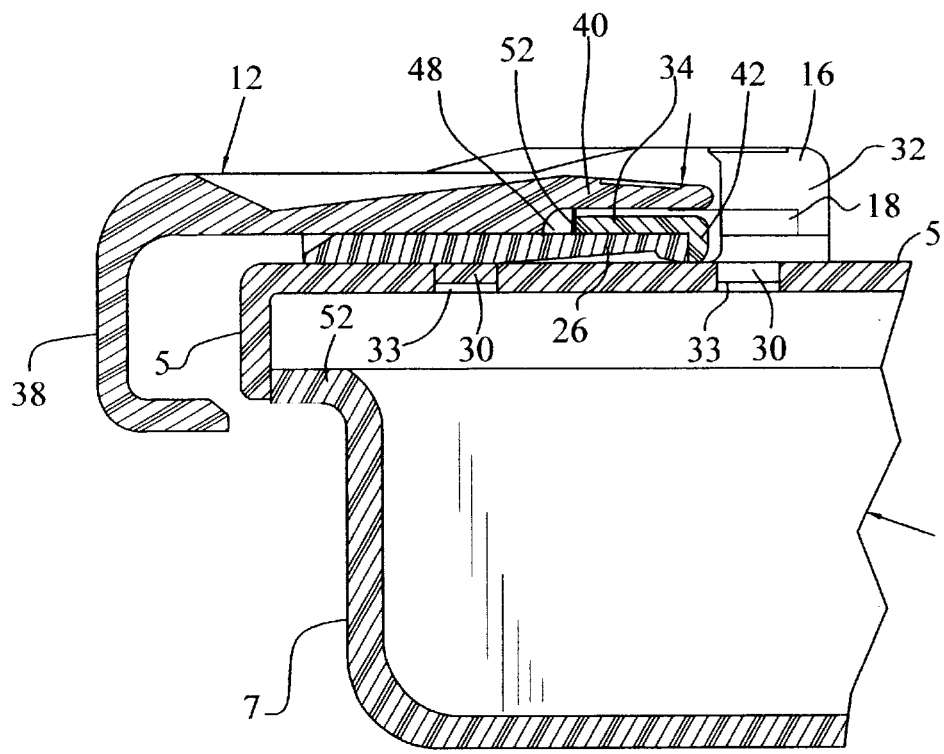
FIG. 7 is a fragmentary sectional view like FIG. 4 but showing the latch mechanism in its open or unsecured position.
Figure 8:
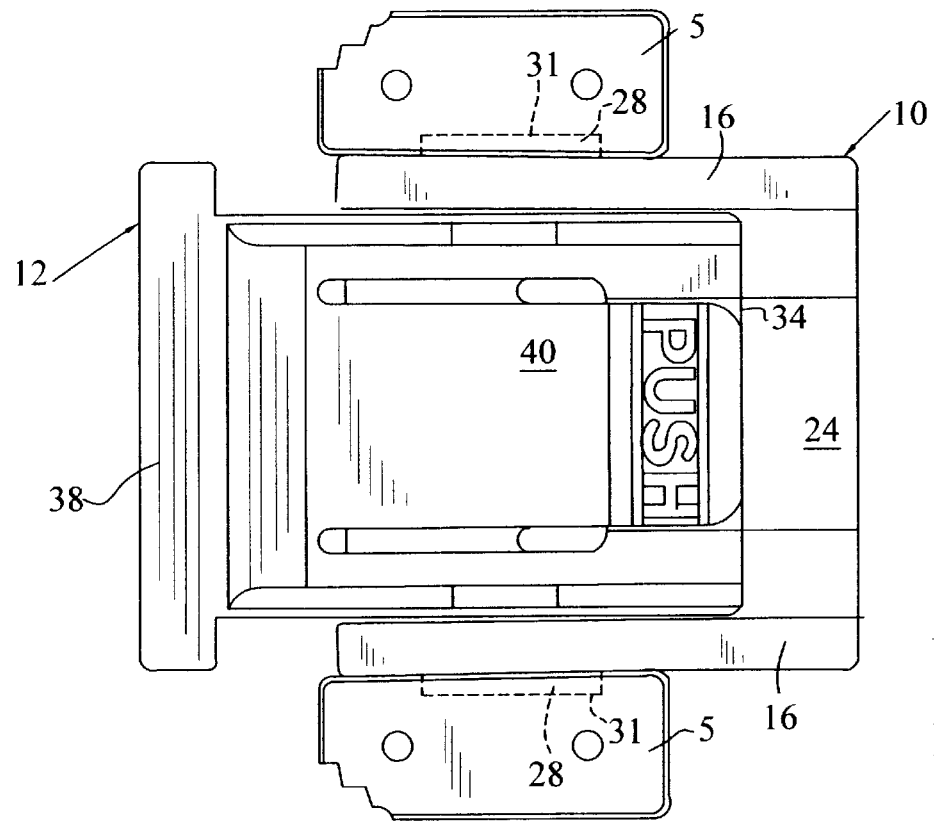
FIG. 8 is a top plan view of the latch mechanism shown in its open or secured position.

With the guide part 10 and slide part 12 now interlocked, the slide part now may be slid relative to the guide part between its open position shown in FIG. 7 and its secured position shown in FIG. 4. Starting in its open position as seen in FIG. 7, slide part 12 is moved rearwardly relative to guide part 10 with ribs 36 being restrictively guided by grooves 18 in their respective parts. During the initial rearward movement of slide part 12 web 34 slides over depressed flap 26 until the slotted opening 48 in the web which accommodates tongue 40 reaches by the flap. At this time, the flap springs upwardly into opening 48 under tongue 40 as illustrated in FIG. 4 with the rearward most edge 50 of the flap 26 fitting adjacently in front of the front edge 52 of web 34 of the slide part so as to provide an abutment which prevents the slide part from being slid forwardly relative to the guide part, thus securing the slide part in its closed position as seen in FIG. 4 with its depending lip 38 extending about the periphery of lid 5 and underlying an out-turned peripheral flange 52 of base 7. In this manner, slide part 12 secures the lid to the base and is interlocked to movement relative to its underlying guide part.

To open the latch mechanism, slide part tongue 40 which is in contact with raised flap 26 is depressed, which causes the flap to be depressed so that its edge 50 is located below edge 52 of the slide part web 34. While still holding tongue 40 in its depressed position, slide part 12 may now be moved forwardly relative to the guide part 10 allowing web 34 to slide over the depressed flap 26 as shown in FIG. 7. This movement of the slide part frees its lip 38 from its underlying engaging position relative to lid 5 and base 7 so as to permit the lid to be removed from the base. When slide part 12 is moved from its open position in FIG. 7 into its closed position in FIG. 4 there is no need to depress or otherwise manipulate tongue 40 since the normally upwardly biased or flexed flap 26, once it clears the underside of web 34 of the slide part will normally spring upwardly into interlocking engagement with the web and with the tongue 44 being in its normally raised position. As slide part 12 interlocks into its closed or secured position as illustrated in FIG. 4, a slight clicking sound will generally be heard as flap 26 springs upwardly and interlocks with web 34.

Guide part 10 and slide part 12 are preferably formed of a plastic composition such as polyphenylsulfone and are of injection molded form. As previously suggested, the latch mechanism parts may be color coded for identification purposes.

The invention is not to be limited specifically to the details above given but may be modified within the scope of the appended claims.

What is claimed is:

1. A container for medical instrumentation comprising a base and an overlying removable lid, a latch mechanism secured to one of said base and lid, said latch mechanism including a guide part attached to said one base or lid and a slide part carried by said guide part shiftable relative to the guide part between a closed position engaging the other of said base and lid to secure the lid to the base and an open position separated from said other from said base or lid to free the lid for removal from the base, said guide part including a flexible flap first catch part, said slide part including a second catch part engaging said first catch part to lock said slide part against movement from its closed position into its open position, said slide part including a depressible tongue release part engagable with one of said first and second catch parts and contacting said first catch part when actuated by depressing said tongue release part to disengage the first and second catch parts and free the slide part for movement from its said closed position into its open position.

2. The container of claim 1, wherein said flap has an upper position engaging said second catch part when said slide part is in its said closed position and a lower position disengaged from said second catch part when contacted by said tongue.

3. The container of claim 2, wherein said flap is upwardly biased into its said upper position to enable the flap to engage said second catch part as said slide part shifts from its open position into its said closed position.

4. The container of claim 2, wherein said guide part is attached to said lid, said slide part including a depending lip, said lip engaging said flap in its said lower position when said slide part is in its open position to prevent separation of the slide part from the guide part.

5. A container for medical instrumentation comprising a base and an overlying removable lid, a latch mechanism secured to one of said base and lid, said latch mechanism including a guide part attached to said lid and a slide part carried by said guide part shiftable relative to the guide part between a closed position engaging the other of by said base and lid to secure the lid to the base and an open position separated from said other from said base or lid to free the lid for removal from the base, said guide part including a first catch part, said slide part including a second catch part engaging said first catch part to lock said slide part against movement from its closed position into its open position, said slide part including a depressible tongue release part engagable with one of said first and second catch parts and contacting said first catch part when actuated to disengage the first and second catch parts and free the slide part for movement from its said closed position into its open position, said guide part including spaced outwardly projecting tabs, said lid including slotted parts, said tabs fitted into said slotted parts to secure said guide part to said lid.

6. The container of claim 5, wherein said guide part includes depending posts, said lid having openings, said posts fitted into said openings when said tabs are fitted into said lid slotted parts.

7. A container for medical instrumentation comprising a base and an overlying removable lid, a latch mechanism secured to one of said base and lid, said latch mechanism including a guide part attached to said one base or lid and a slide part carried by said guide part, said slide part shiftable in its entirety relative to the guide part between a closed position engaging the other of said base and lid to secure the lid to the base and an open position separated from said other base or lid to free the lid for removal from the base, wherein said guide part is attached to said lid, said guide part including spaced outwardly projecting tabs, said lid including slotted parts, said tabs fitted into said slotted parts to secure said guide part to said lid.

8. The container of claim 7, wherein said guide part includes depending posts, said lid having openings, said posts fitted into said openings when said tabs are fitted into said lid slotted parts.

9. A container for medical instrumentation comprising a base, an overlying removable lid, and a latch mechanism secured to one of said base and lid, said latch mechanism including a guide part attached to one of said base or lid, a slide part carried by said guide part and shiftable relative to the guide part, and a depressible tongue for contacting a flexible catch part when said tongue is depressed to release said latch mechanism from a closed position securing the lid to the base to an open position, said catch part being a flexible flap, which when so contacted by said tongue moves and is thereby disengaged from a second catch part, wherein said depressible tongue is located on said slide part and said flexible catch part is located on said guide part.

10. The container of claim 9, wherein said flap is upwardly biased into an upper position to enable said flap to engage said second catch part as said slide part shifts from an open position into said closed position.

11. The container of claim 10, wherein said guide part is attached to said lid, said slide part including a depending lip, said lip engaging said flap in a lower position when said slide part is in its open position to prevent separation of the slide part from the guide part.

12. The container of claim 9, wherein said guide part has spaced apart opposing grooves, said slide part including parallel ribs fitted slidably into said grooves.

13. The container of claim 9, wherein said guide part is attached to said lid, said guide part including spaced outwardly projecting tabs, said lid including slotted parts, said tabs fitted into said slotted parts to secure said guide part to said lid.

14. The container of claim 13, wherein said guide part includes depending posts, said lid having openings, said posts fitted into said openings when said tabs are fitted into said lid slotted parts.

* * * * *